US006101886A

United States Patent [19]
Brenizer et al.

[11] Patent Number: 6,101,886
[45] Date of Patent: Aug. 15, 2000

[54] MULTI-STAGE SAMPLER CONCENTRATOR

[75] Inventors: Jack S. Brenizer, Charlottesville; Charles E. Daitch, Arlington; Bouvard Hosticka, Charlottesville; L. Roger Mason, Jr., Arlington; Pamela M. Norris, Charlottesville, all of Va.

[73] Assignees: Pacific Sierra Research, Arlington; University of Virginia Patent Foundation, Charlottesville, both of Va.

[21] Appl. No.: 09/199,979

[22] Filed: Nov. 25, 1998

Related U.S. Application Data

[60] Provisional application No. 60/066,592, Nov. 26, 1997.

[51] Int. Cl.[7] .................. G01N 1/04; B01D 39/00; B01D 50/00; B01D 45/08

[52] U.S. Cl. .................. 73/863.23; 73/863.22; 73/863.25; 73/864.71; 55/308; 55/321; 55/325; 55/442; 55/446

[58] Field of Search .................. 73/863.22, 863.23, 73/864.71, 863.25; 55/421, 442, 446, 308, 321, 325

[56] References Cited

U.S. PATENT DOCUMENTS

| | | | |
|---|---|---|---|
| 3,662,765 | 5/1972 | Clark | 55/522 |
| 4,387,603 | 6/1983 | Nelson | 73/863.22 |
| 4,570,494 | 2/1986 | Dunn et al. | 73/863.22 |
| 4,584,867 | 4/1986 | Forster | 73/31.05 |
| 5,343,767 | 9/1994 | Marple et al. | 73/863.22 |
| 5,360,572 | 11/1994 | Hotaling et al. | 252/181.6 |
| 5,470,612 | 11/1995 | Hotaling et al. | 252/181.6 |
| 5,618,493 | 4/1997 | Goldstein et al. | 73/31.02 |
| 5,693,895 | 12/1997 | Baxter | 73/863.23 |
| 5,725,836 | 3/1998 | Rouanet et al. | 423/462 |
| 5,864,923 | 2/1999 | Rouanet et al. | 23/295 R |
| 5,911,658 | 6/1999 | Yoldas | 252/62 |

*Primary Examiner*—Hezron Williams
*Assistant Examiner*—Chad Soliz
*Attorney, Agent, or Firm*—John E. Wagner; Robert C. Smith; Sam Bernardo

[57] ABSTRACT

Atmospheric Samplers are disclosed using aerogel filter material. The samplers include one or more cascaded impact sample stations with discs of aerogel as the targets. Ambient air carrying particulate matter is introduced into the sampler and the particles are captured by the aerogel in its pore structure. In certain embodiments, the aerogel filter is next transported to a position where it is fragmented by a spray of water. The fragmented aerogel and the captured particles are transported in the fragmenting water from the sampler for analysis. In one embodiment, the sampler is segmented with alternate nozzle and filter segments for easy assembly, sampling and disassembly for analysis of the captured particles in aerogel filters positions below the nozzles.

5 Claims, 9 Drawing Sheets

FIG. 1
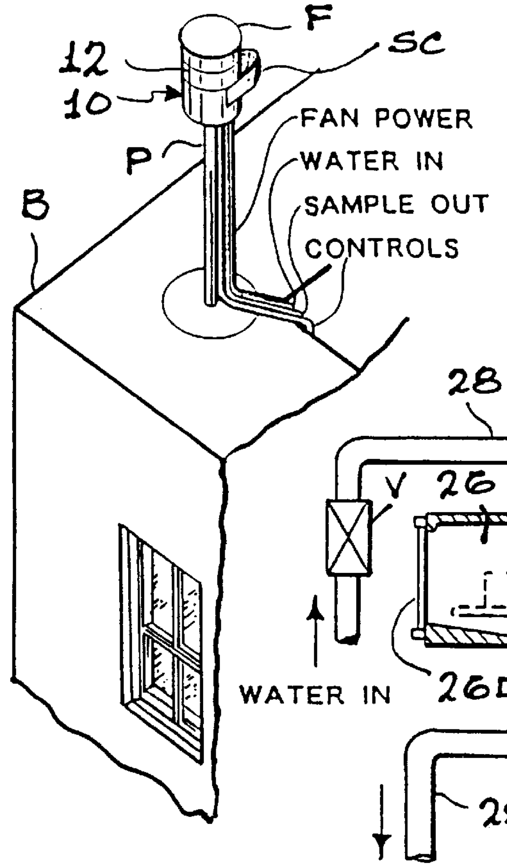
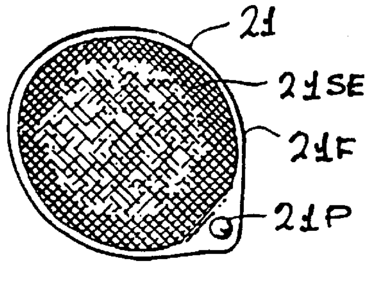
FIG. 2C
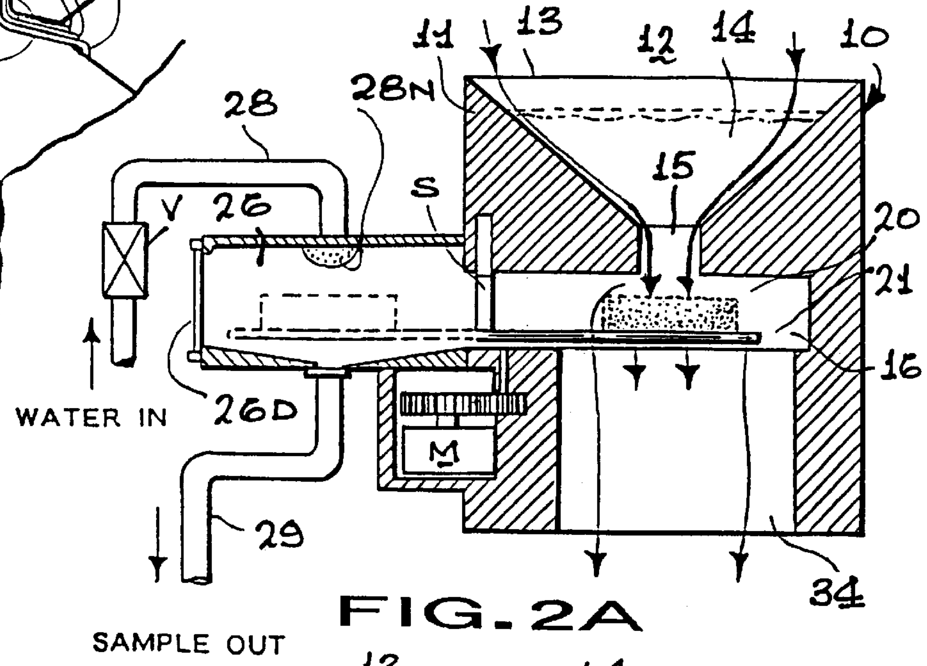
FIG. 2A
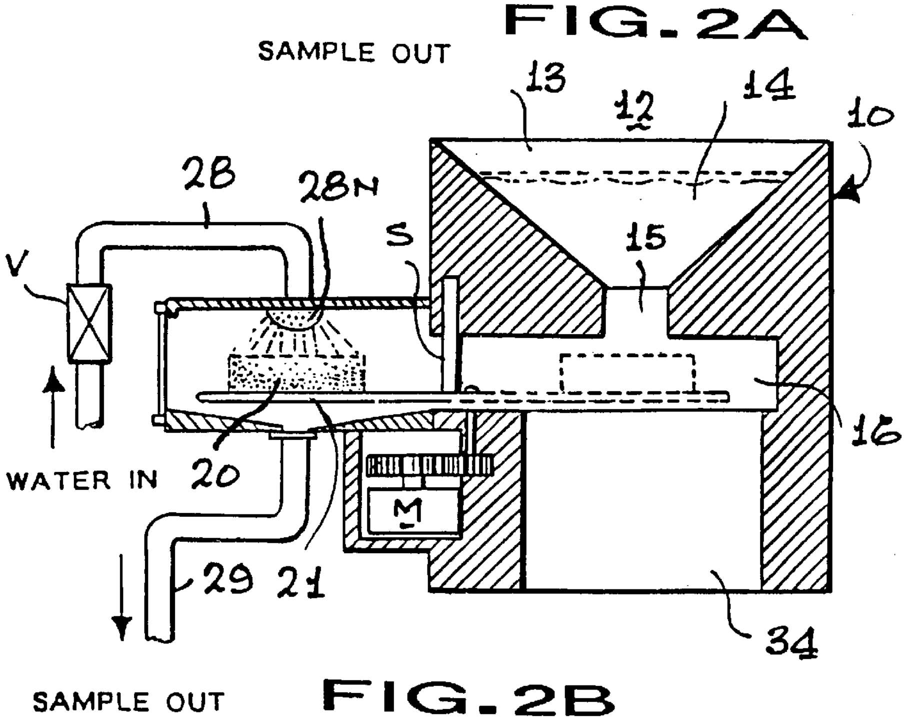
FIG. 2B

FIG. 9
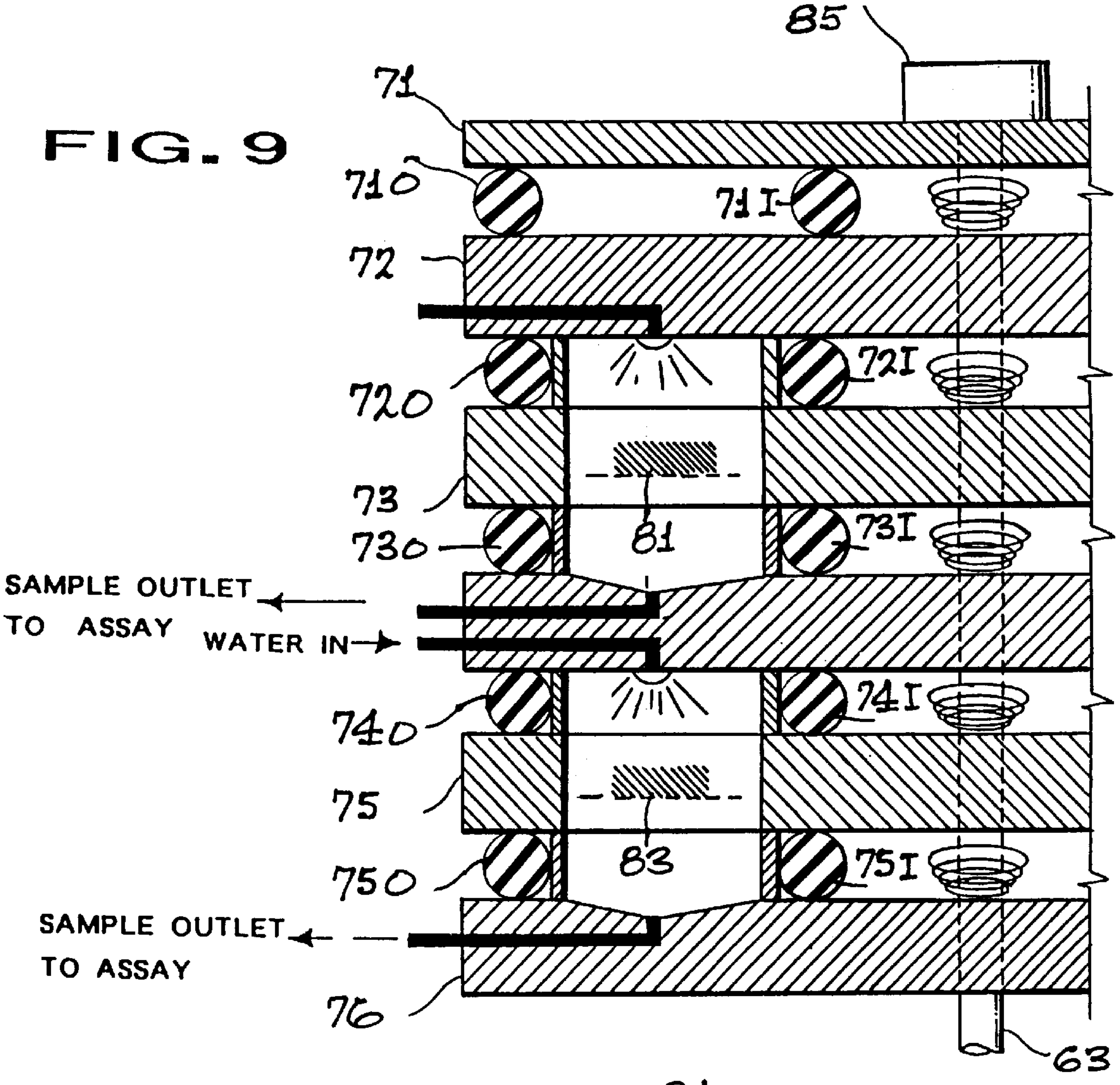
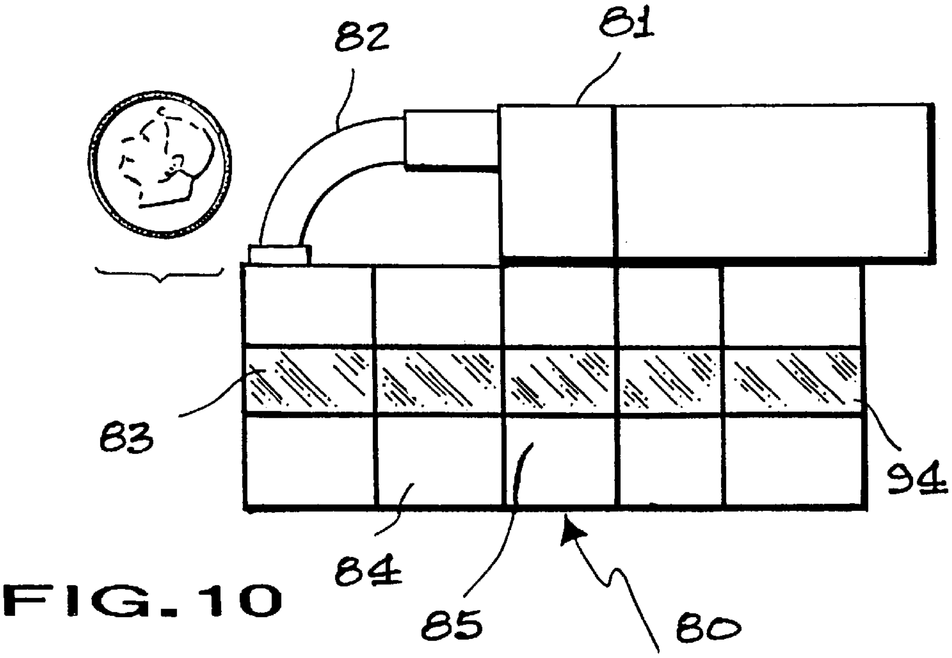
FIG. 10

MULTI-STAGE SAMPLER CONCENTRATOR

REFERENCE TO RELATED APPLICATIONS

This is a non-provisional application based upon the Provisional Patent Application, Serial No. 60/066,592, filed Nov. 26, 1997 for AEROGEL ENVIRONMENTAL SAMPLER AND CONCENTRATOR, for which the original filing date is claimed for this application, and a related Provisional Patent Application, Serial No. 60/070,279, filed Dec. 30, 1997 for SMART AEROGEL, now International application 41/827826, filed Dec. 29, 1998, the contents of which are incorporated by reference, herein.

U.S. GOVERNMENT SPONSORED RESEARCH/ DEVELOPMENT

Work under which this invention was made was sponsored in part by the U.S. government under contracts:

1. Contract Number DAAH01-97-C-RO92, awarded by the U.S. Army Aviation and Missile Command, AMSAM-AC-RD-A, Redstone Arsenal, Ala. 35898-5280.
2. Contract Number MDA972-97-C-0020, awarded by the Defense Advanced Research Projects Agency (DARPA), Contracts Management Directorate (CMD), 3701 N. Fairfax Drive, Arlington, Va. 22203-1714.

BACKGROUND OF THE INVENTION

The detection of airborne contaminant, particulate, flora or biologicals or the like is a continuing and expanding need to minimize health risks to populations. Rapid detection of the presence of such contaminants is essential to taking effective steps for population protection. This need requires remote collection, concentration and assay of samples on a real time basis. It is also imperative that biological materials, which may be collected, are protected from fragmentation during the collection and concentration steps to avoid mistaken analysis of the sampled biological material.

Therefore, it is essential that the collection step be accomplished in a filter medium or other collector, which does not alter the sample collected. Transfer from the collector to a concentrated sample must not alter the sample in any manner, which would degrade the assaying operation. Likewise, the concentration or preparation step, which is usually essential to efficient transportation to the assay operations, cannot destroy the specimen sought to be analyzed.

The bio-efficiency of any such system also is of prime importance and includes the bio-efficiency of the inlet aspiration, the bio-efficiency of the transmission chamber and the bio-efficiency of the collection medium used. The aspiration efficiency is primarily determined by the inlet geometry. The transmission efficiency is primarily determined by the sampling line or the transmission chamber, which connects the inlet to the sampling medium. This is ideally very short. The collection efficiency is most dependent upon the properties of the filter medium used.

Heretofore, to the knowledge of the inventors, no one has achieved an efficient self-contained air sampler capable of collecting airborne contaminants, concentrating them and conveying them for immediate assay into a multifunctional material.

Examples of previous attempts to achieve efficient samplers may be seen in the following United States patents U.S. Pat. No. 4,301,002 HIGH EFFICIENCY VIRTUAL IMPACTOR Nov. 17, 1981

Billy W. Loo Assignee: U.S.A., Dept of Energy

U.S. Pat. No. 4,391,151 CIRCULAR TWO-STAGE PARTICULATE AND GAS SAMPLER Jul. 5, 1983

Nelson et al Assignee: PIXE International Corp.

U.S. Pat. No. 4,640,140 AEROSOL SAMPLER WITH CASCADE IMPACTION AND UNIFORM DEPOSITION Feb. 3, 1987

Burghoffer et al Assignee: Comm. A l'Energie Atomique (France)

U.S. Pat. No. 4,677,864 SYSTEM FOR AUTOMATIC SAMPLING SAMPLE CONVEYANCE FOR ANALYSIS Jul. 7, 1987

Inv. Gluschenko et al Assignee: V.N-I I K. I. T. (U.S.S.R.)

U.S. Pat. No. 5,404,763 POLYPORT ATMOSPHERIC GAS SAMPLER Apr. 11, 1995

S. F. Guggenheim Assignee: U.S.A. Dept. of Energy

U.S. Pat. No. 5,691,487 COUPLING OF AIR SAMPLES TO A SAMPLER Nov. 25, 1997

Inv. Green et al Assignee: Tekmar Company

U.S. Pat. No. 5,831,182 REMOTE SAMPLING DEVICE FOR DETERMINING Nov. 3, 1998

Inv. E. A. Swenson, unassigned

None of the foregoing samplers, however, provide the features of this invention.

BRIEF DESCRIPTION OF THE INVENTION

Faced with the foregoing state of the art, it occurred to us that it is possible to design an impaction filter of graduated or controlled pore size as the primary collector. We felt that we could use the desirable properties of selected aerogels to provide a collector/concentrator for air borne particulates for assaying by a suitable analyzer.

The aerogel materials of interest are those having a complex pore structure including micropores, (1–10 nm) and mesopores (100–500 nm); high porosity (>98%); extremely high internal surface area (1500 m2/g) and the ability to be reduced to a liquid by a simple aqueous process. These multi functional properties are integrated into a collection device that enables the collection, separation and concentration of aerosols.

One object of this invention is to design an environmental air sampler that utilizes the fundamental advantages of aerogel materials. The baseline design is a generic collection subsystem, which provides a capability to separate bioaerosols from large volumetric air samples, sample preparation, and delivery of the sample to the assay subsystem.

The samplers are intended to provide large volume air sampling, multiple particle size discrimination, and sample preparation for assay. It incorporates a common sampling motif utilizing impactor plates; impaction theory is well known and effective in separating particles of varying mass, usually with multiple stages. Particle laden air is drawn into the sampler via a blower or pump.

Next, the particles are accelerated through a nozzle towards an impactor plate maintained at a fixed distance from the nozzle. The plate deflects the flow creating fluid streamlines around itself. Due to inertia, the larger particles are impacted (collected) on a collector plate which in this case is an aerogel disc body while the smaller particles follow the streamlines into a successive impaction chamber.

The subsequent nozzle and aerogel body can be selected to collect a smaller class of particles. This process can be iterated to collect a specified number of particle classes; this is also known as cascade impaction. By continuously passing air through the cascade impactor, the particles can be concentrated to many times the original air concentration before collection.

The second stage of a sampler usually involves sample preparation where the collected analytes are removed from the impactor plates via liquid washes followed by transport to a detector for identification, or directly transported as a solid sample to a detector.

Incorporating aerogel into our system design benefits both functions of the sampler: collection and sample preparation. Aerogel discs mounted on screen supports are used as impactor plates. Using aerogels, we believe that the impaction efficiency can be enhanced with aerogel's high porosity by reducing recoil and detraining losses. Aerogel's ultra high surface area also enhances collection efficiency by increasing the amount of sample retained, thus providing a more concentrated sample for assay. Aerogel benefits sample preparation because of its unique ability to break down under aqueous conditions. Thus, aerosol particles can be directly collected by an aerogel plate followed by immediate liquid reduction to a concentrated sample for analysis or the aerogel sample can be directly analyzed as a solid. The inorganic silica aerogel matrix will not interfere with the analysis of the desired bio-organic molecules. Thus, the characteristics of aerogels of being frangible and subject to fragmentation by water facilitates the analysis of the particles collected in the aerogel.

One sampler built demonstrates the possible uses of aerogels as an aerosol sampling media. The aerogels employed were made with phase separation techniques that created large pore structures. Aerogel impactor discs which we have designated Standard Rx acted as the impactor stage collectors while a different type of aerogel, designated EB08, had the necessary combination of large pores for high flow rate and structural integrity to allow constituent filter discs to be made from the material. Both types exhibit the frangible characteristics of aerogels.

In accordance with this invention, volumetric air samples are collected by the sampling device after prefiltering of large particles (>500 nm). The particulates are then separated from the incoming air by impaction using the complex bimodal pore structure of the aerogel pore structure to target discrete particle size distributions. The large internal surface area of the aerogel can also be doped in accordance with the teaching of the copending patent application for SMART AEROGELS, referenced above, to make the aerogel pathogen specific. In such case, the aerogel is doped during the synthesis process with collection enhancing compounds or sample preparation mixtures to aid in the subsequent assay.

The aerogel selected also is formulated to be hydrophilic so that it is extremely hygroscopic to ambient water vapor collected but the water vapor does not damage the matrix structure. The aerogel also responds to liquid water which completely fractures the aerogel matrix and the aerogel and its collected biological material are easily reduced to an aqueous suspension in a readily sampled form. This liquid reduction process is used to concentrate the aerosols into several milliliters of solution to increase the assay sensitivity.

Several forms of samplers are disclosed including:

a. a single stage collector/concentrator;

b. a multi stage collector with individual concentrator stations;

c. a multi stage multi station sampler which can take multiple samples periodically by advancing a series of sampler stations into collection positions and then to concentration positions; and d. a miniature cascade impactor employing aerogel filter elements.

In certain cases it has been found to be desirable to separate the sampling and collection functions from the reduction step. In this situation, the miniature cascade impact collector of paragraph d., above is recommended. It is made up of a number of cylindrical sections including an intake section, nozzle sections, and filter sections, each of which is removable, interchangeable and exhibiting the same collection efficiencies as the other more complex samplers.

BRIEF DESCRIPTION OF THE DRAWING

This invention may be more clearly understood from the following detailed description and by reference to the drawings, in which:

FIG. 1 is a perspective view of an installation of this invention;

FIG. 2A is a simplified vertical sectional view of a single stage air sampler in accordance with this invention in its collection condition;

FIG. 2B is a simplified vertical sectional view of the single stage collector of FIG. 2A with the aerogel filter moved into a concentration or sample preparation position;

FIG. 2C is a top plan view of the filter support and transfer device of FIGS. 2A and 2B;

FIG. 9 is an enlarged vertical fragmentary sectional view of the portion of the rotating filter assembly of FIGS. 4 and 5 in a concentration mode and taken along lines 9—9 of FIG. 4;

FIG. 10 is a side elevational view of a miniature particle collector and air pump in accordance with this invention shown with a United States dime for size comparison;

DETAILED DESCRIPTION OF THE INVENTION

Figure 5:
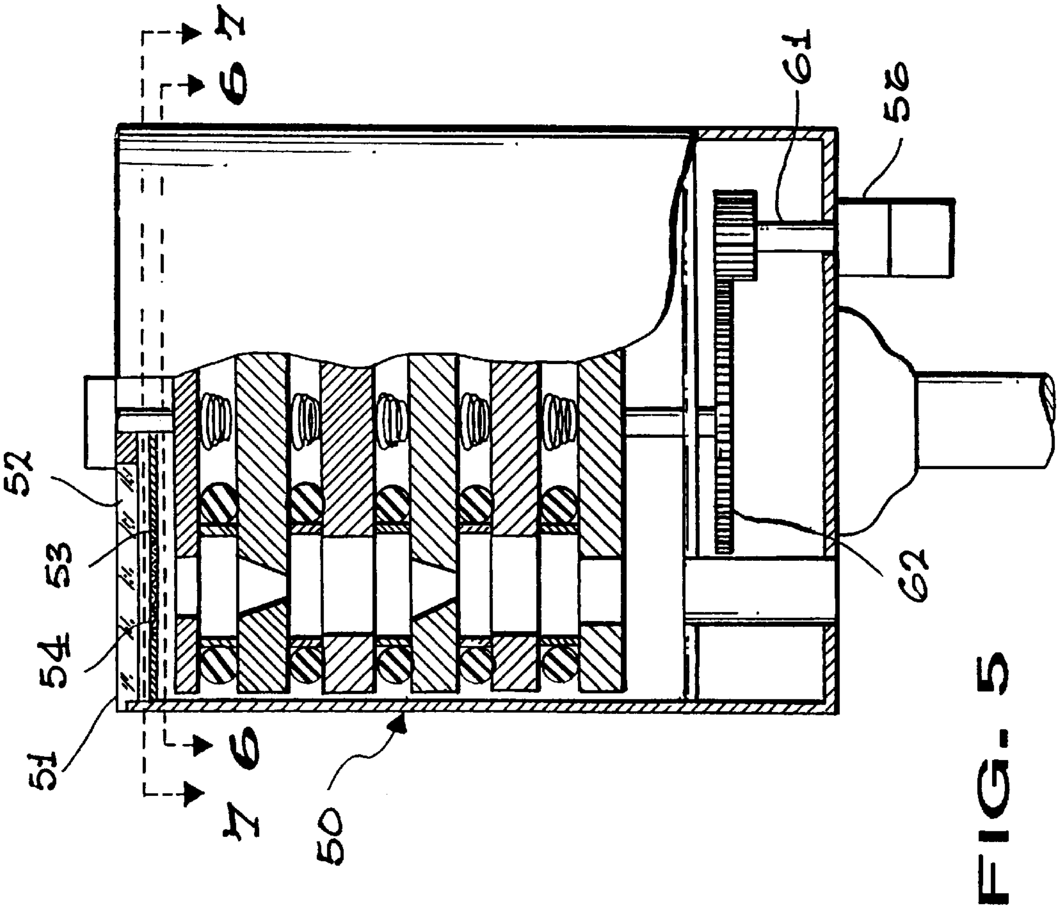
FIG. 5 is a side elevational view of the sampler of FIG. 4 with portions broken away and with the internal collector in vertical section to show one set of multiple stage filters in a sampling or collecting position.

The need to monitor air quality continues as a requirement for not only gaseous contaminants but submicron particles and organisms, as well. FIG. 1 shows a typical installation of an air sampler, generally designated 10, of this invention on a building B and supported on a post P with the sampler 10 appearing as an upstanding cylinder and side chamber SC with an opening therein for receiving incoming air drawn in by either ambient air movement or a fan F shown as mounted on top of the sampler 10. Air is introduced into side ports and flows through the sampler 10 to be exhausted through the bottom of the sampler.

For an understanding of the sampler 10 of this invention and its method of sampling, reference is now made to FIGS. 2A, 2B, 2C, and 2D. FIGS. 2A–2D show an example of a single stage single sampling system. Later drawing figures show multiple stage multiple sample systems.

SINGLE STAGE SAMPLER CONCENTRATOR

Now referring to FIG. 2A which is a longitudinal diametrical sectional view of a single-stage aerosol collector 10, including a collector body 11 having an input opening 12 into which omnidirectional flow of air is introduced such as fan A of FIG. 1 and unshown in FIG. 2. In other applications may be from ram air input of the collector 10 is mounted on a moving vehicle.

The opening 12 includes a pre-filter 13 of opening sizes typically 4 micrometers to 6 micrometers for separating ambient dust and flora from the incoming air which is then drawn through conical nozzle 14 and its throat 15 to enter the first virtual impactor volume 16 in which particles of sufficient mass impact upon and are captured in the pores of a first aerogel filter 20 resting on a cantilevered pivotal screen support 21. Particulate of lesser mass and the major portion of the incoming air, travel around the aerogel filter 20, before discharge through outlet 34.

The virtual impactor volume 16 is closed on one side by an airtight shutter S which is shown in its lowered or closed position but is moved to an upper or open position when the collection operation is completed and closed again for the sample preparation operation as shown in FIG. 2B and discussed below. The shutter S seals the collection chamber 16 from a sample preparation chamber 26.

Figure 2D:
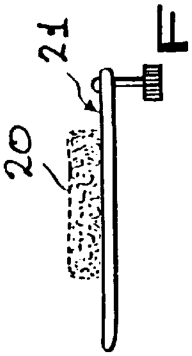
FIG. 2D is a side elevational view of the transfer mechanism of FIG. 2A with an aerogel filter in place.

The screen support 21, best seen in FIGS. 2C and 2D includes a frame 21F, screen 21SC and pivot opening 21P. The screen support 21 is supported on shaft 21SH of FIGS. 2A and 2B to be rotated by motor M and its associated gearing of FIGS. 2A and 2B from its collection position of FIG. 2A, 180 degrees to the preparation position of 2B. Of course, other means for moving the screen 21 are readily available to mechanical designers.

The preparation chamber 26 includes a spray nozzle 28N fed by a water line 28 from a purified water source, unshown, via a valve V and also includes a sample out line 29 to the bioassay stage. Door 26D closes the preparation chamber 26 and allows access for inserting a replacement aerogel filter 20.

METHOD OF OPERATION

In sequence, shutter S is operated to OPEN or UP position, motor M is operated to move the screen support 21 into the preparation chamber 26. Door 26D is opened, an aerogel filter is placed on the screen support 21 and the door 26D closed. The motor M is operated to return the screen support to its filtering position and shutter S is closed.

Airflow is introduced into the sample 10 for a predetermined period of time for an adequate sample to be taken. Airflow is terminated, shutter S is opened, the sample carrier 21 is moved to the preparation chamber and positioned below the spray head or nozzle 28N. The shutter S is closed and a fine spray of water directed to the entire top surface of the aerogel filter 20 gently fragmenting it and leaving it in a water suspension and allowing the suspension of the collected biological materials to flow into the line 29.

Any biologics have thus been subjected only to impaction on a low mass filter and then introduced into an aqueous carrier by the mild step of reducing the low mass filter to a minute volume of the collected spray water.

Next, the assay step may begin immediately from line 29. Meanwhile, a new filter is introduced onto the carrier 21 after through drying of the preparation chamber 26 and the collection chamber 16. The new filter 20 and its carrier 21 are returned through the opening between the two chambers 26 and 16 (with shutter S open) and then after closing shutter S, the next sample may be taken.

Figure 3:
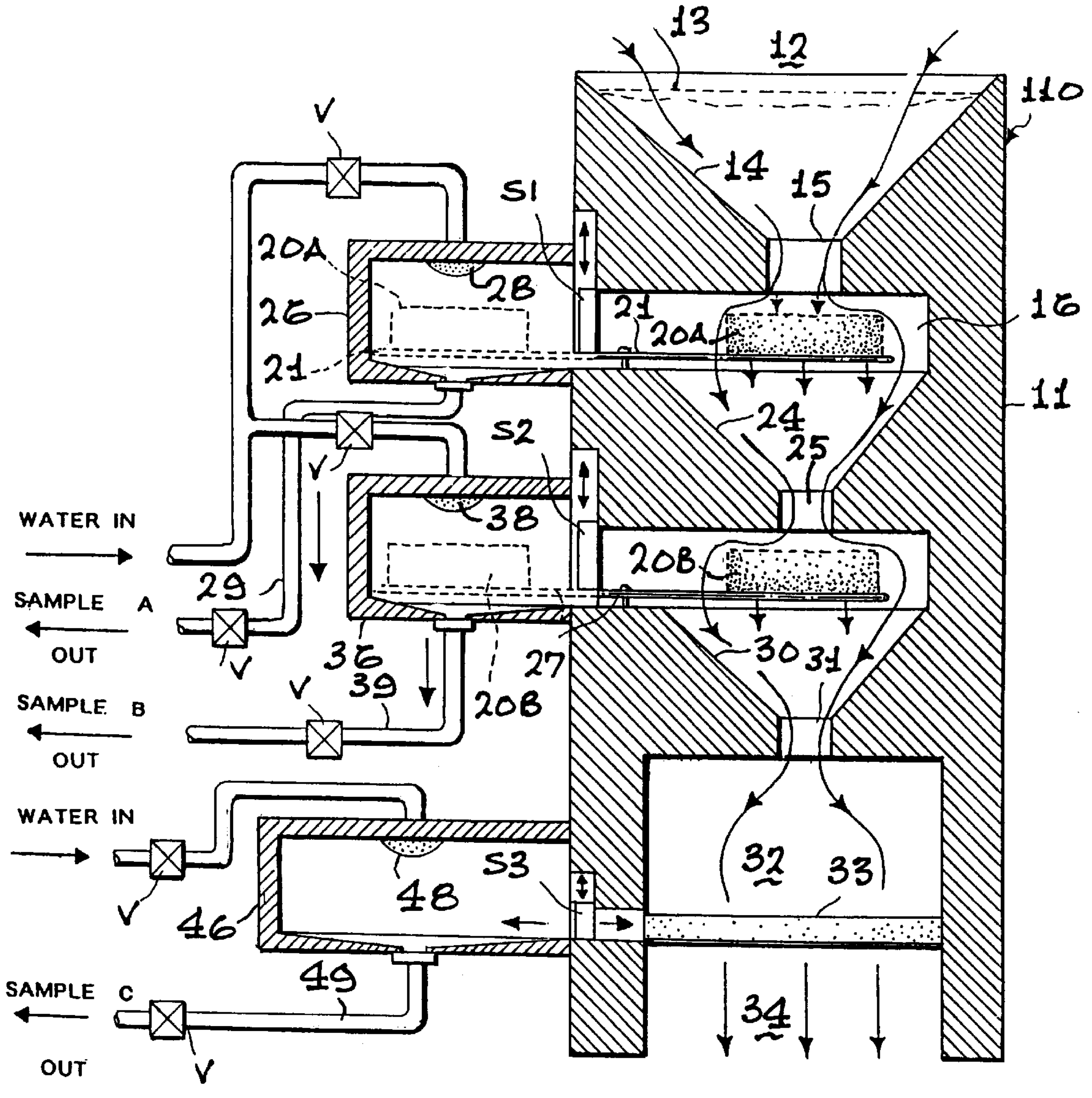
FIG. 3 is a vertical sectional view of a multi-stage filter aerosol collection of this invention shown in a multiple sample collection condition.

Reference is now made to FIGS. 2 and 3, which are diametrical vertical sectional views of a multistage sampler 110 similar to sampler 10 but containing three stages of filtering after the pre-filter 13. All devices identical to those of FIGS. 2 and 3 bear the same reference numerals.

In the embodiments of FIGS. 2 and 3, intake air at opening 12 passes pre-filter 13 enters nozzle 14 and passes through its throat 15 and selected coarse particulates impact on and are captured in aerogel filter 20A. Air passing through filter 20A and the air and particulate of lesser mass pass around filter 20A and into the next nozzle 24 and its throat 25 to impact on the second filter 26 in its virtual impactor chamber 16A. Aerogel filter 20B has a different, e.g., smaller pore size to capture at least one additional sample size. The aerogel impactor 20B rests on its rotatable screen support 27. The lighter particulate matter and air pass around this second stage sampler continues through nozzle 30 and throat 31 to the chamber 32 and a filter 33.

A third filter 33 in chamber 32 may be of the aerogel type or other filter medium. As shown in FIG. 3, filter 33 is also shown with a preparation chamber 46, nozzle 48 and sample collection line 49 as well as a shutter S3.

Each of the collection chambers has their sidewall closed by a shutter S1, S2 or S3, respectively. These shutters seal their respective chamber collection during sampling. Shutters S1, S2 and S3 may be opened by actuators, unshown, to allow transfer of the aerogel 20, 26 or filter 33 each with its sample into their respective liquid reduction modules 26, 36 and 46.

Transfer of aerogel filters 20A, 20B, and 33 may be accomplished by any of several means. In this case, as an example, each aerogel filter 20A, 20B and 33 rests on a respective support 21, 27 or 31 which is basically a perforated screen with an edge ring as is shown in FIGS. 2C and 2D mounted for pivotal movement into their associated liquid reduction module 26, 36 or 46.

Other forms of transfer mechanisms, for example, a sliding support rather than a rotating support, may be used. As shown in FIG. 3, the doors or shutters are shown in their lower or CLOSED condition to close each sampling chamber during impacting and capture of particulates and organisms of interest.

After cessation of air flow and opening of shutters S1, S2, and S3 transfer of samples into their respective liquid reduction module, and closing of shutters S1, S2 and S3, each sample is separated into a stream of analytical grade pure water by a spray of a few milliliters from spray head 28, 38 or 48. The particulate and sampled material of any type collected is then suspended in the water and conveyed by the respective SAMPLE OUT conduits 29, 39 and 49 to the analytical apparatus used for assaying the samples.

Each of the different aerogel filters is ideally selected with different pore size or other characteristics to capture different particulates or organisms.

MULTI STAGE MULTI TIME PERIOD SAMPLER

In many applications there is a need for semiautomatic or automatic sampling of the air at regular intervals over a period of time. This can be accomplished in accordance with another embodiment of this invention.

Figure 4:
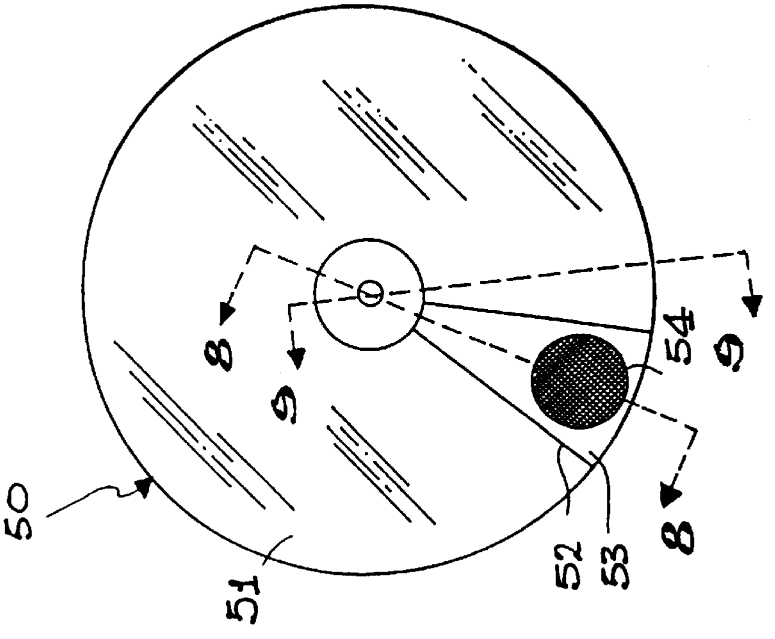
FIG. 4 is a top plan view of a multiple stage, multiple sampler embodiment of this invention.
Figure 6:
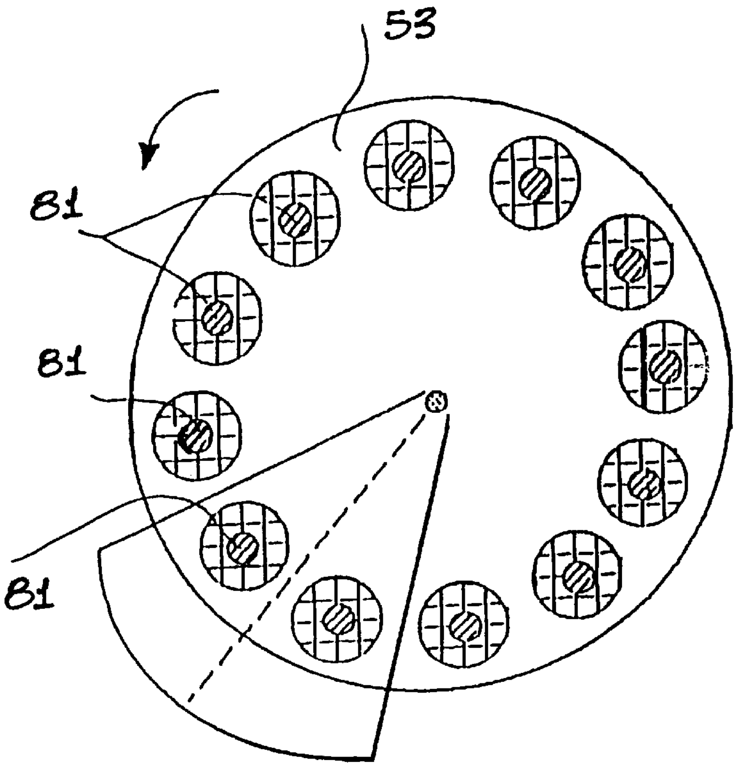
FIG. 6 is a horizontal sectional view of the sampler of FIGS. 4 and 5 taken along lines 6—6 of FIG. 5.
Figure 7:
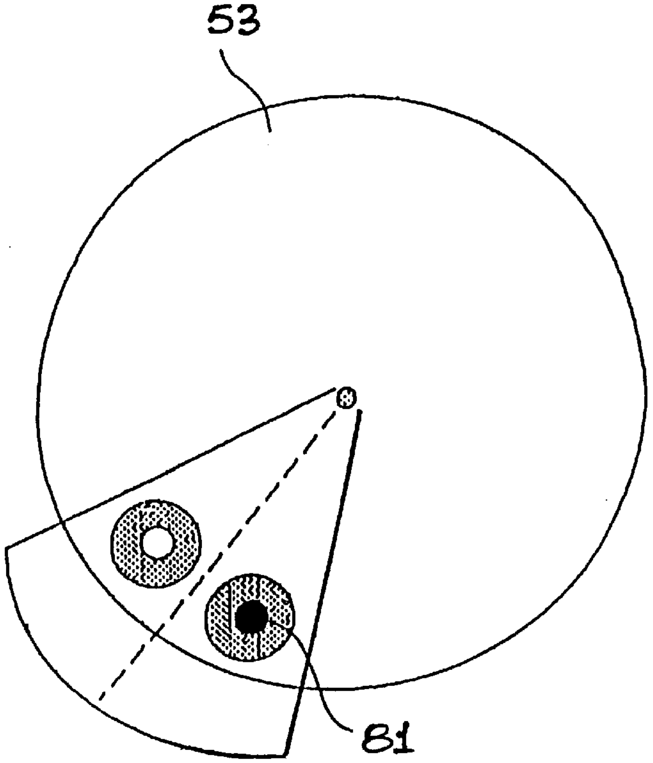
FIG. 7 is a horizontal sectional view of the sampler of FIG. 4 taken along lines 7—7 of FIG. 5.
Figure 14:
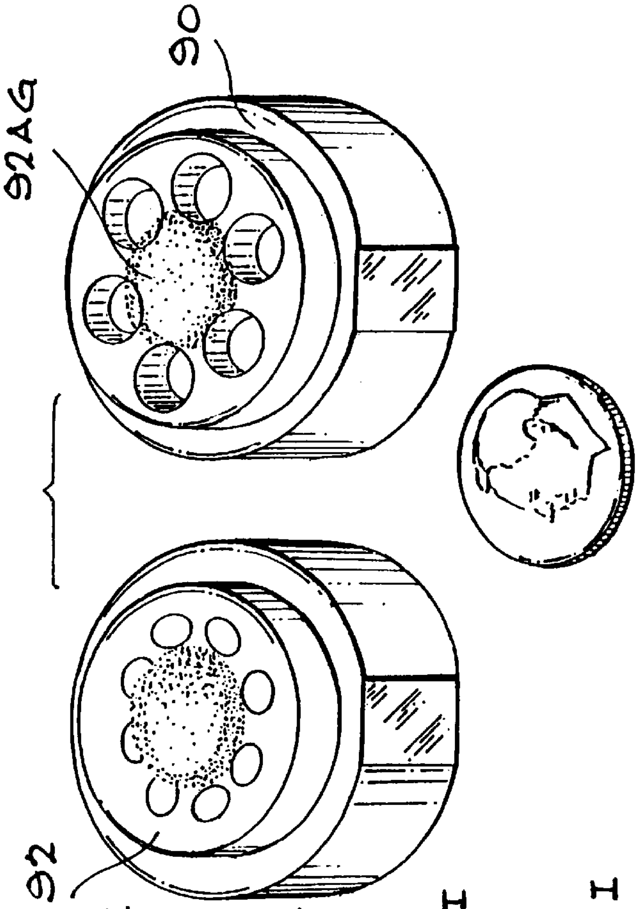
FIG. 14 is a perspective view of two of the elements of the particle collector of FIG. 10 with a United State dime to show the relative size of the element.

Now referring to FIG. 4 in combination with FIGS. 5–7, a miniature environmental air sampler is shown therein which provides large volume air sampling, multiple particle size discrimination and sample preparation into solution for assay. It incorporates a multiple sample design using impactor plates in multiple stages including a wash or preparation solution station for fragmenting or dissolving each sample aerogel filter and entraining its sample for transfer to a separate assay or analysis station outside of the collector.

In addition to multiple stages of collection as is disclosed in FIGS. 3A and 3B, the sampler of FIGS. 4–7 includes a plurality, e.g., 12 separate sample receivers, each of multiple separation capability. By a rotation of 30 degrees, a new sample set is brought into position to extract airborne particulate and organisms and introducing the sample into an aqueous solution for analysis. This system is ideal for periodic sampling.

FIG. 4 shows the top view of a multiple sample collector 50 having a cover plate 51 with a V shaped opening 52 which exposes one segment of a rotating aerogel collector plate 53 of FIG. 6 carrying a series of pre-filters 54 of FIG. 4. The pre-filters 54 are selected with an opening size selected to capture particulates of 5 micrometers or larger size. Such particulates are not usually of interest for this sampling system and need to be removed from the samples. The collector plate 53 is rotatable in angular increments to expose a new sample collector and to advance the previous sampling stage to the wash or sample preparation stage.

In the example shown in FIGS. 4–7, twelve aerogel filters 81 are used and therefore periodic samples at twelve different times may be taken before reloading the sampler 50.

FIG. 5 shows a side view of the sampler of FIG. 4 with its sidewall 55 partly broken away to show a simplified form of rotator assembly of FIGS. 8 and 9, described below. The housing 50 includes an externally mounted stepper motor 56 with its drive shaft 60 carrying a spur gear 61 driving a speed reduction gear 62. Reduction gear 62 drives the main shaft 63 of the rotating collector assembly 57 in 30 degree increments.

Figure 8:
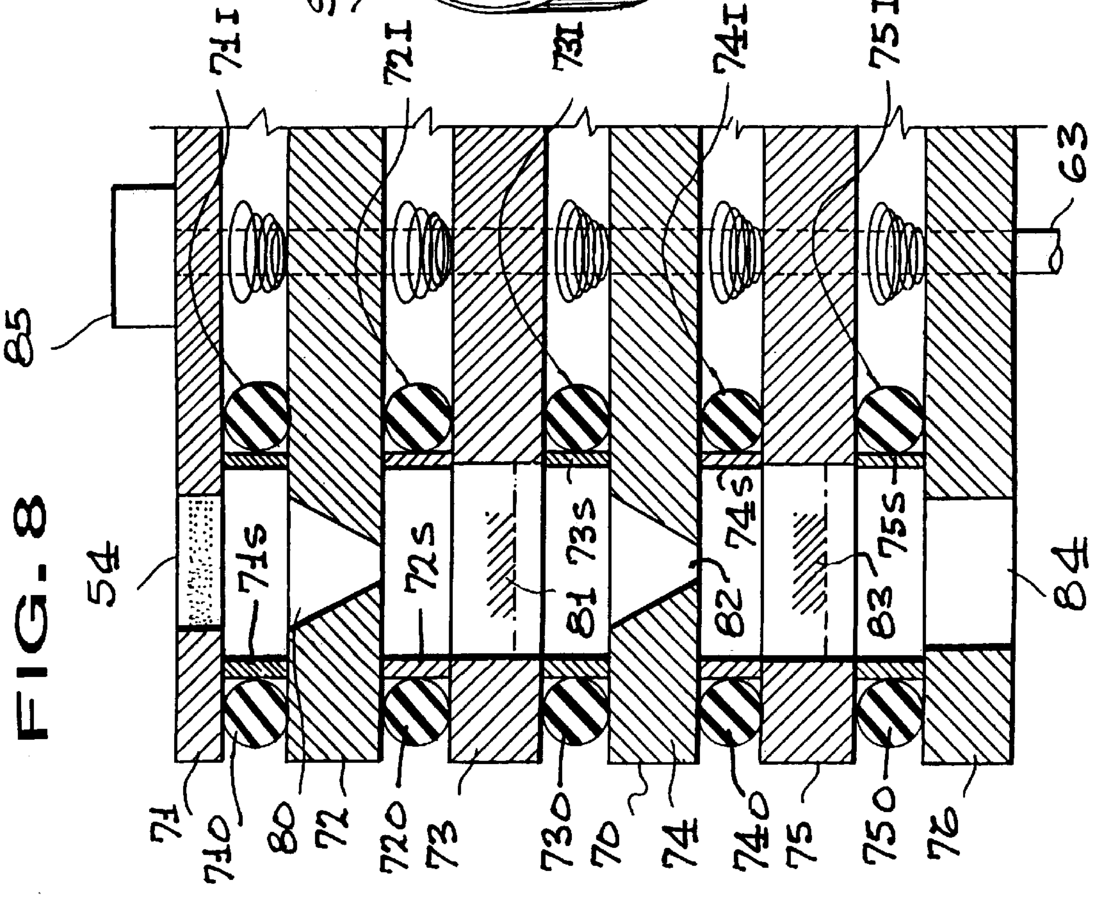
FIG. 8 is an enlarged vertical fragmentary sectional view of a portion of the rotating filter Assembly of FIGS. 4 and 5 taken along line 8—8 of FIG. 4.

The collector assembly, best seen in FIGS. 8 and 9, generally designated 70, comprises, basically, a plurality of stacked spring loaded rotatable plates 71–76 on the common shaft 63 with two concentric O rings, the outer O rings 71-O through 75-O located between adjacent plates, e.g., the outer O ring 71-O is located between plates 71 and 72, etc. The O rings 71-O through 75-O act as an outer seal for the collector assembly 70. A set of inner O rings 71-I through 75-I act as inner seals for the sampling zone which fall between the outer O ring and the inner O ring at each stage between adjacent plates.

In order of operation with air flow in at the top of the stack, air flows through the pre-filter 54 supported in an opening in plate 71 to remove unwanted larger particulates and the pre-filtered air next flows through nozzle 80, aerogel filter 81, nozzle 82, second stage aerogel filter 83 and then to exit 84. Sleeves 71S–75S confine the flow through each stage, which limit the airflow to a downward direction through the sampler, and isolates each of the several sampling filter stacks from each other. The plates are each secured to the central post or shaft 63 by the clamp 85 or by any of several types of securing means such as swaging or by pins, to allow the stack of plates to be driven in unison by the stepper motor 56.

Upon operation of the stepper motor 56 for one increment of travel, e.g., 30 degrees, the sampling set shown in FIGS. 5–8 is rotated to the wash or sample preparation position shown in FIG. 9 where the two aerogel filters are each exposed to water spray from their respective water inlets to fragment the aerogel and allow collection of the aerogel filter entrapped particulates and samples of interest into an aqueous stream to their analysis station outside of the sampler 50 where an assay is conducted. At the same time that the sample collected aerogel filters have moved to the wash or solute station, the next set of filters and their associated nozzles has moved into place below a new pre-filter ready for sampling. After a full cycle of twelve sampling and wash or aerogel filter fragmentation operations, the sampler is ready for removal, cleaning and installation of new aerogel filters and return to its sampling environment.

Altogether, we have utilized the ideal characteristics of aerogels to produce a simple but effective air sampler and method of operation. Of importance to many applications of air sampling is the fact that the aerogel filter allows precise particle size selection by pore size of the aerogel and nearly automatic collection of all captured samples in a minuscule amount of water with the filter material dispersed in the liquid sample. There is reduced danger of disruption of the material collected as the filter just disperses after fragmentation from around it. Therefore, fragile samples should be preserved in their state as captured in the filter. The fact that only a small amount of water is used means that the assay sample is small, with a high concentration of the captured material of interest.

Employing this invention, below is a tabulation of recommended aerogel materials, pore size, and typical airborne particulates which may be collected:

| Aerogel Type | Pore Size | Biological Material |
|---|---|---|
| Filter 20 | 1 | Bacteria |
| Filter 20A | | Rickettsia |
| Filter 20B | | Virus |
| Filter 33 | | Toxins |

Work on aerosol collection in the development of this invention has been concentrated in determining the suitability of aerogels as impaction surfaces. To this end, the aerosol generating equipment has been configured to generate monodispersed aerosols in the 0.5 to 2 micron range. The main characteristics under consideration are aerosol collection efficiency, particle penetration, and ablation of the aerogel surface. Impaction plates are made from either thin cast aerogels or thin pieces machined from larger castings. These are mounted on glass cover slips for ease of handling using double sided tape. The thickness (usually about 1 mm) is then measured to allow the nozzles of the impactor to be adjusted to maintain an optimum separation between the nozzle and the collection surface.

Qualitative studies using dry aerosols performed by examining bounce-off from the primary impaction surface using a reverse cascade indicate that (as expected) aerogels perform as well as most other dry impaction surfaces. By using a very shallow depth of focus on a microscope and taking advantage of the transparent nature of the aerogel, the penetration of particles and ablation can be measured to within a few microns by moving the microscope stage vertically with a micrometer while observing features coming into focus at various heights. As a test of this technique, imperfections of the aerogel surface were measured as well as some interesting sub surface artifacts such as bubbles and "layer lines".

Microscopic examination of the impaction surfaces after aerosol collection while using jet velocities that are selective for 700 nm particles (55 m/s), shows that there is no discernable ablation of the surface nor significant penetration of one-micron particles into the surface. The particles are captured directly under the nozzle in a heap as well as in small surface imperfections some distance from the nozzle. However, because the surface is dry, there is no wicking of a new surface over the collected particles so that once the aerogel beneath the jet is covered with particles, new aerosol particles collide with the previously collected particles and bounce off of the surface. Due to the many surface imperfections of a cast aerogel, there is an opportunity to re-collect these bounce-off particles as the air stream passes over the surface.

Studies throughout the this development project indicated that the standard recipes developed for aerogels with small pore sizes and transparency would not permit gas flow through the gel at rates high enough to be useful as samplers. Thus a new line of aerogels was used investigated that were made with phase separation techniques that created large pore structures (macropores). Of the several materials tested, only one type of aerogel designated EB08 described below had the necessary combination of large pores, for high flow rate and structural integrity to allow constituent filter disks to be made from the material.

The collection efficiency of aerogel EB08, to date, is not spectacular, however, in a sampling system designed to detect the presence or absence of certain specific particles or pathogens, collection efficiency is not the controlling criteria for success. Using ambient air as the source of aerosols, the ambient air was analyzed and found (as usual) to consist mostly of particles around 100 nm diameter. The best gross collection efficiency demonstrated to date is 97% at 180 cc/min (normalized as above), Flow rates may increase to higher levels such as 320 cc/min, as an indication that new flow paths are established (cracks or other leaks) and the gross collection efficiency can drop, for example into the range of 92% or thereabouts. Broken down into various size groups, typical collection efficiencies have been observed:

15 nm: 99%
25 nm: 96%
40 nm: 88%
75 nm: 76%
134 nm 68%

Below is a graphical representation of collection efficiency for the aerogel EB08, the characteristics of which are set forth below:

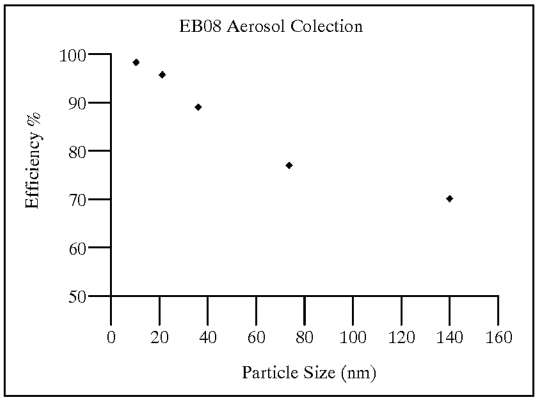

The strong bias toward the small end of the particle distribution indicates that the collection mechanism is diffusion of particles to the walls of the pores, However due to the increased flow indicating a possible leak, not too much weight should be applied to this.

Aerogels EB08, as produced, are easily machined to consistent sized disks of 25 mm by three mm thick which are self supporting and robust enough to survive mechanical mounting as demonstrated by pressing the sample itself between two O-rings without any scaling compound. The differential pressure at 1.5 liters per minute of such disks is only 2.5 kPa. All of these attributes make Aerogel EB08 a suitable filter material for through-flow application in the samplers of this invention.

| | Aerogel Standard Rx | Aerogel EB08 | Ratio EB08/Std Rx |
|---|---|---|---|
| Gas Permeability (cmˆ2/s) | 0.001 | 20 | 2 × 10ˆ5 |
| Surface Area (mˆ2/cmˆ3) | 68 | 320 | 4.7 |
| Porosity (%) | 97 | 76 | 0.78 |
| Average Pore Size | 0.025 | tens | hundreds |
| nm Collection Efficiency | Complete | 92% (biased small) | 0.92 |

MINIATURE SAMPLER

In the cases cited above where only the collection and concentration of particulates is required at a particular location and reduction followed by analysis or assaying is performed elsewhere, the embodiment of FIGS. 10–15 is appropriate.

Figure 11:
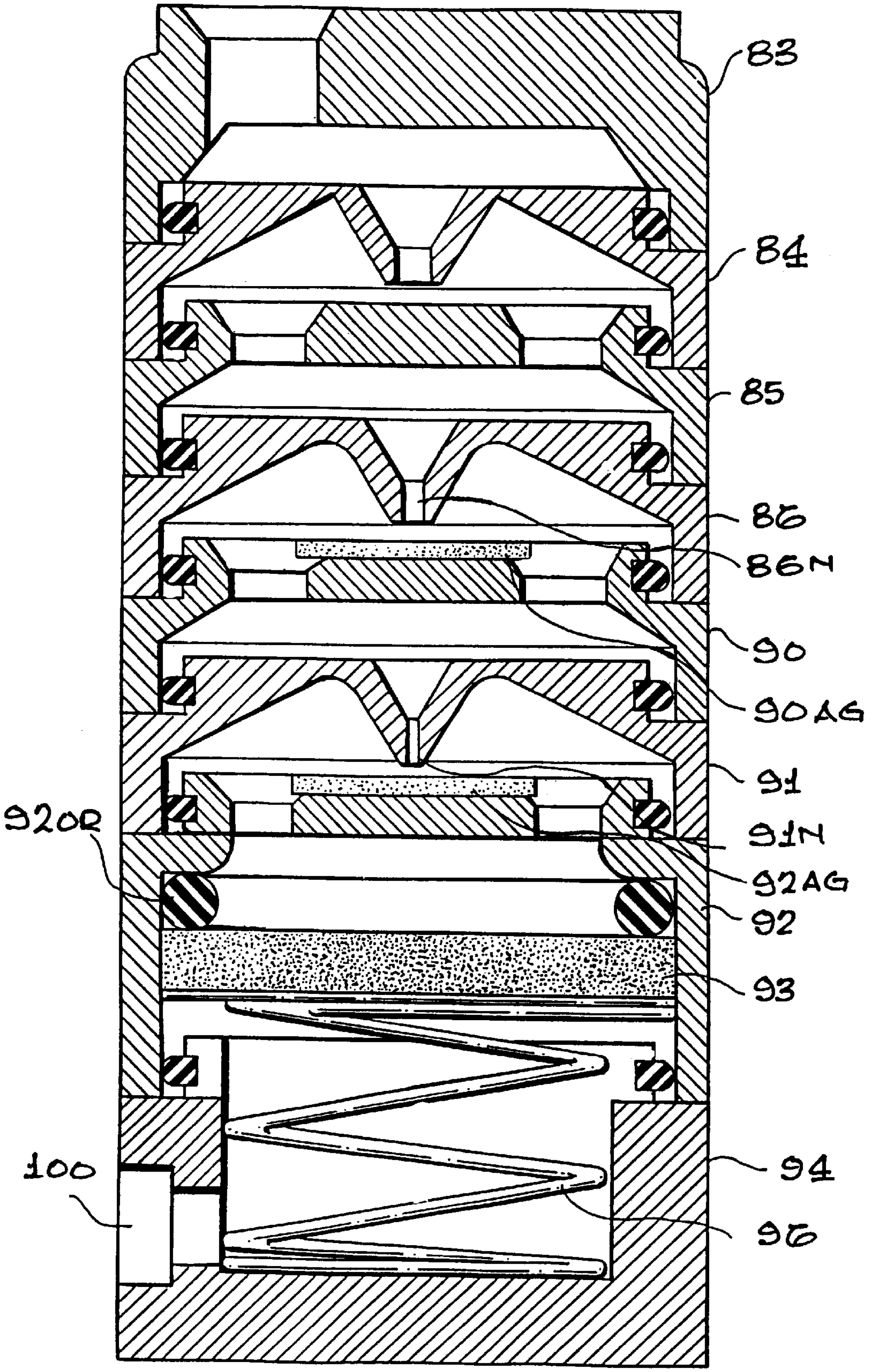
FIG. 11 is a longitudinal diametrical sectional view through the particle collector of FIG. 10.
Figure 12:
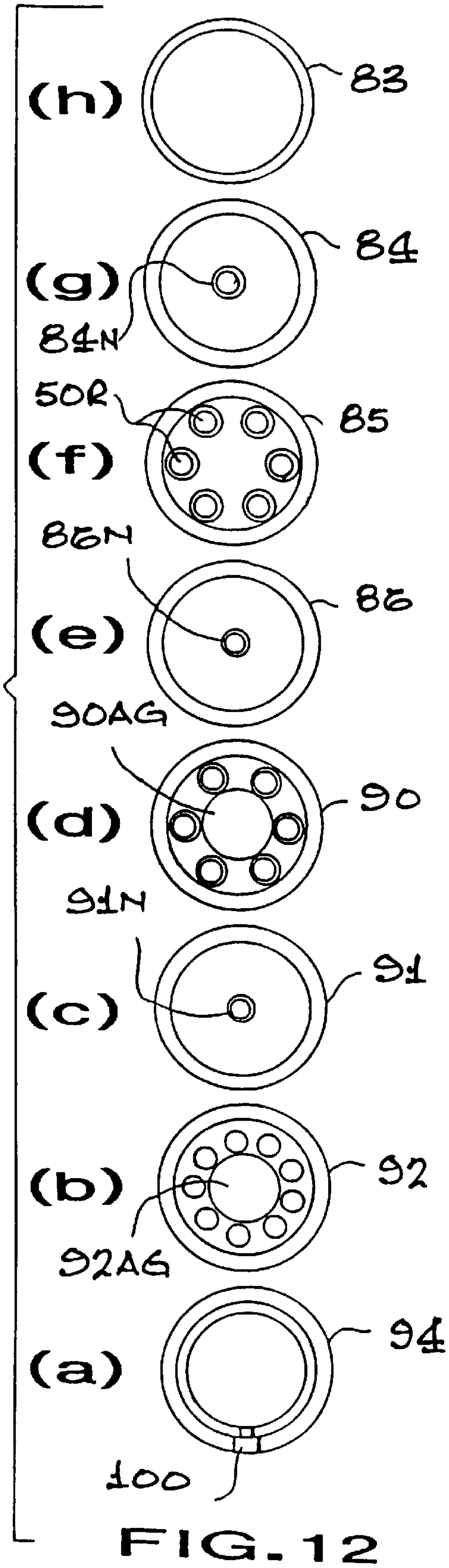
FIG. 12 is a top plan view of each of the elements of the particle collector of FIGS. 10 and 11.
Figure 13:
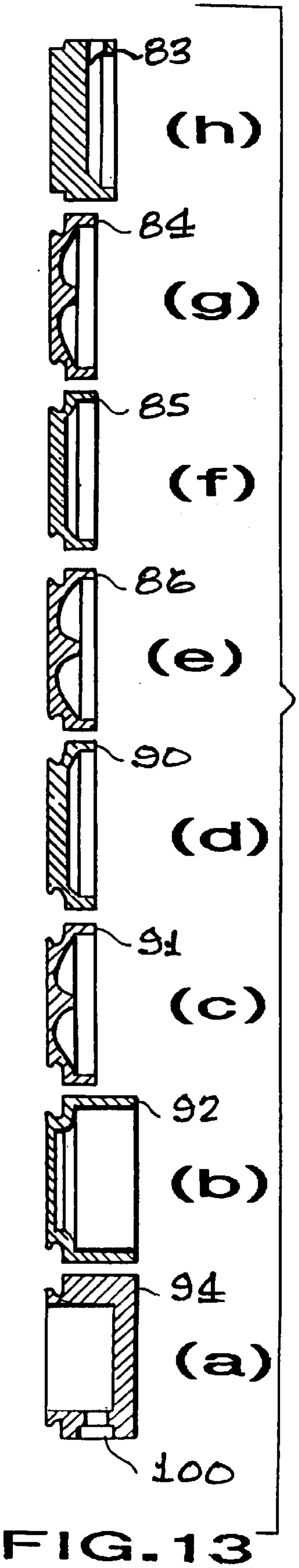
FIG. 13 is a series of diametrical sectional views through each of the elements of FIG. 12.
Figure 15:
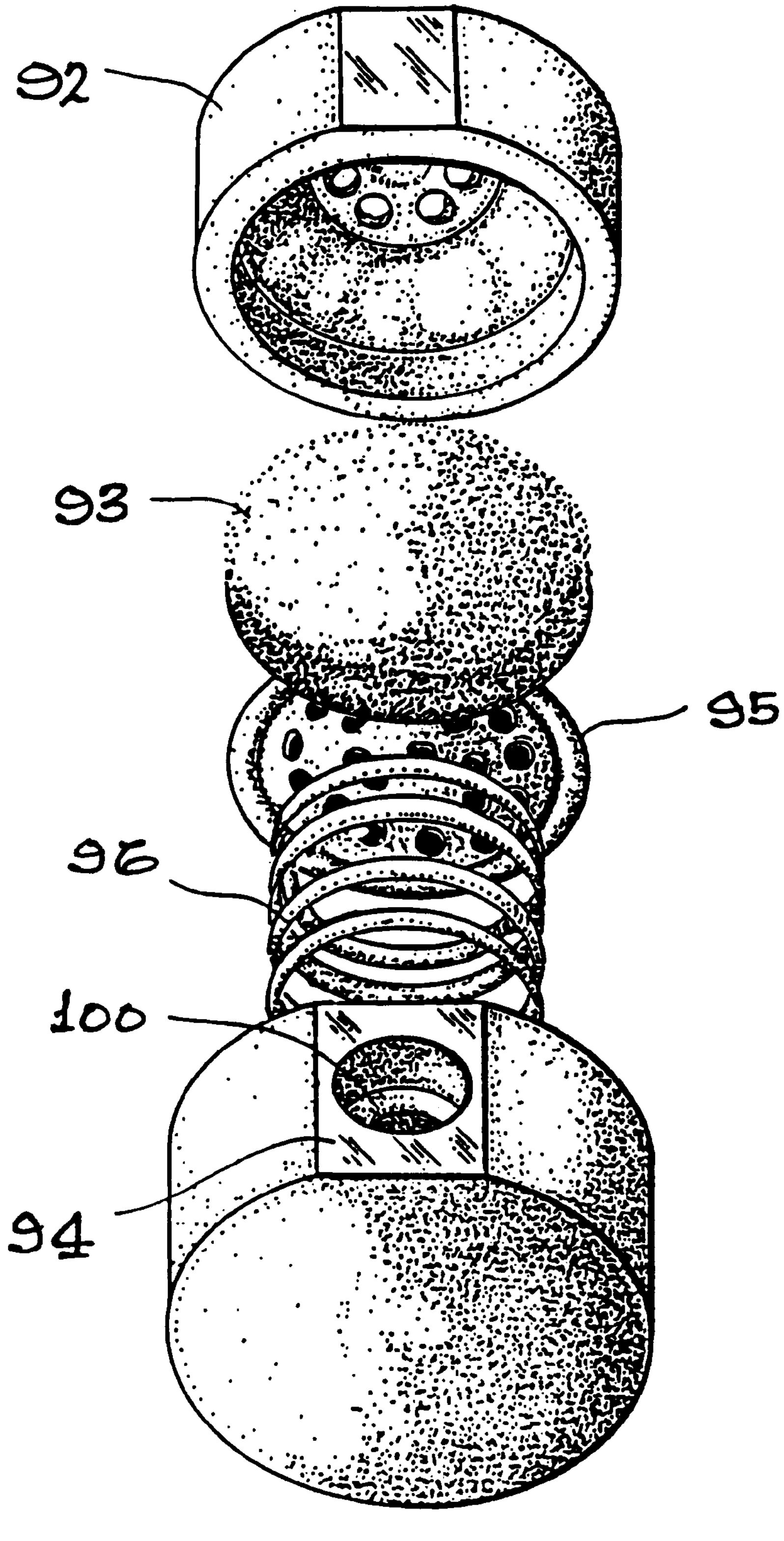
FIG. 15 is an exploded view of the base and the filter element of the particle collector of FIG. 10.

Now referring to FIG. 10, in combination with FIGS. 11 and 12, a miniature sampler, generally designated 80 which includes three impact stages, two of which use aerogel impactors and one an aerogel filter. The sampler 80 constitutes a cylindrical body made up of eight sections which are secured together during operation and may be disassembled by the removal of securing means such as longitudinal machine screws or external clamps. Attached to the side of the sampler is a vacuum pump 81, which is electrically driven as by a 12v-d.c. source.

The pump 81 provides air flow in the order of 1.5 liter per minute through tube 82 to an inlet stage or manifold 83 which precedes a first nozzle stage 84 which precedes a pre-filter or diffusion stage 85 having an array of six peripheral orifices, 85OR. As shown in FIGS. 11 and 12, the stage 85 includes only the orifices without any pre-filter similar to filter 13 of FIGS. 2 and 3 so its function is to diffuse the flow through the first nozzle 84N of stage 84. A second nozzle stage 86 directs the stream of air through its nozzle 86N directly onto an aerogel impactor disc 90AG of the first impactor stage 90 which is also shown on the right hand side of FIG. 14.

The third nozzle stage 91 with its nozzle 91N is located immediately above the second aerogel impactor stage 92 with its aerogel impactor 92AG supported in a recess in the upper surface of the second impactor stage 92. The underside of the second impactor stage 92 is hollow and mounts an O ring 92OR which bears on the upper edge of an aerogel filter disc 93. The second impactor stage rests on the base or outlet stage 94 including a cavity 95 therein used to retain a spring 96 which biases the aerogel filter 93 against the O ring 92OR in position for the aerogel filter to provide the final stage of collection in the sampler 80. Exhaust air exits the sampler through outlet 100 in one side of the base 94. The second impactor stage 92 and the base section 94 with the filter 93 and its biasing spring 96 and filter support may also be seen in the exploded view of FIG. 15.

A general description of the miniature sampler 80 of FIGS. 10–15 is that it includes of up to three impaction stages, two of which use our standard Rx aerogel discs as collectors and a final stage using a EB08 aerogel disk as a flow through filter. Flow through the sampler 80 is driven by a miniature 12 volt vacuum pump 81. The flow rate is 1.5 liters per minute, conventional, and pre-concentrators such as cyclone concentrators or virtual impactors could be used in conjunction with this final sampler to allow larger flow rates to be sampled.

The three impactor stages have a calculated 50% cut size of 1.9 microns, 0.8 microns and 0.36 microns. The size of the collected spot of the two smaller sizes (the standard aerogel stages) is less than 1 mm. The collection sizes were chosen for demonstration and testing purposes and can be easily adapted to particular needs.

The first impactor stage is designed to remove large dust particles (if no interest, while the second and third stages are designed for fairly high collection efficiencies at 1.0 and 0.5 microns respectively, The aerogel collectors are 1 mm thick and up to 12 mm in diameter. These can be either cut from larger pieces or specially cast to that size. As previously noted, the rough surface of the aerogel allows some secondary collection of particles that bounce off of the primary impact spot.

Tests of the second stage with 0.998 micron florescent latex beads as the test particulars in a 50% relative humidity air stream show collections efficiencies between 66% and 79% relative to a glass impinger (defined as 100%). Overall the sampler 80, with all stages in use is a cylinder 30 mm in diameter and 75 mm tall. The air pump 81 supplying the requisite air flow is a similar cylinder of 29 mm. by 72 mm. high.

Sampler 80 Characteristics:
Flow Rate: 1.5 L/m.
Impactor 50% Cut Size (Calculated)
Stage 1: 1900 nm
Stage 2: 770 nm
Stage 3: 360 nm
Spot size: Stage 2 and 3: approximately 1 mm

| Pressure Drop: | |
|---|---|
| Stage 1: | 0.5 kPa |
| Stage 2: | 3 kPa |
| Stage 3: | 17 kPa |
| Filter: | 0.1 kPa |
| Total | 20.6 kPa |

Electrical:
9 volts DC
0.12 amps
1.1 watts
Dimensions:
Sampler:
30 mm diameter
75 mm high
Pump:
29 mm diameter
72 mm high
Inlet/Outlet ¼ inch OD tubing
Nozzle Diam:
#1(84N) 1.5 mm
#2(86N) 0.85 mm
#3(91N) 0.55 mm
Aspect ratio: 1:1 (ratio of nozzle diameter to spacing between nozzle tip and impactor plate)
Thickness of aerogel impactor plate: 1 mm.
Maximum diameter of aerogel plate 13 mm.
Size of EB08 Filter (93):
25 min diameter
3 mm thick
Performance Tests:

Glass Impinger is regarded as 100% collection efficiency for the 1000 nm particles. The below data is referenced to the Glass Impinger.

Stage 2 collection efficiency at 1000 nm is approximately 70% over 5 minutes which represent about 3 million particles over the course of a single run.

Stage 3 collection of 1000 nm beads bouncing off from stage, 2 is approximately 15% of the total number of beads EB08 aerogel filter 93 performance at various sizes:
135 nm 68%
75 nm 76%
40 nm 88%
25 nm 96%
15 nm 99%

This strong bias towards high efficiency at small sizes indicates that the collection for small particles is dominated by diffusion.

The foregoing embodiments are merely representative of the various ways of carrying out this invention. It is recognized that one of skill in the sampling art might produce other embodiments without departing from the spirit and substance of this invention as set forth above. Therefore, the true scope of this invention is to be judged only by the scope of allowed claims in this patent application including the added protection afforded to the inventors under the Doctrine of Equivalents.

What is claimed is:

1. A sampler for particles contained in a fluid comprising:

an elongated body including an inlet for fluid containing particles the presence of which is to be detected and an outlet for discharge of the fluid after removal of detected particles;

said body comprising a plurality of removable segments constituting the sampler;

at least one of said segments defining a nozzle for directing the fluid to the next succeeding segment;

at least one of said segments being apertured and mounting a body of frangible aerogel filter material subject to fragmentation when exposed to a spray of liquid in the flow path of the fluid through the apertured segment;

at least said apertured segment being separable from the remaining segments for access to said body of frangible filter material for removal of said filter material and any particles collected therein and for replacement of the body of frangible filter material.

2. A sampler for particles contained in a fluid in accordance with claim 1 further comprising a plurality of nozzle defining segments and a plurality of apertured segments, each mounting a body of frangible aerogel filter material subject to fragmentation when exposed to a spray of liquid arranged in alternating sequence to provide a series of particle collecting stations from a stream of fluid passing through said sampler.

3. A sampler in accordance with claim 1 wherein said apertured segments mount their respective body of frangible filter material in front of the adjacent nozzle and each of said apertured segments includes additional apertures therethrough to allow a portion of the fluid from the adjacent nozzle to pass around the body of frangible filter material.

4. A sampler in accordance with claim 1 including a filter positioned in said sampler before said outlet; said filter extending across the entire fluid flow path before said outlet to sample particles remaining in the fluid flowing through the sampler after passage through the previous segments.

5. A sampler in accordance with claim 4 wherein said filter is made of aerogel material subject to fragment by water.

* * * * *